(12) United States Patent
Buckberry et al.

(10) Patent No.: US 11,583,618 B2
(45) Date of Patent: *Feb. 21, 2023

(54) METHOD OF HEAT SANITIZATION OF A HAEMODIALYSIS WATER CIRCUIT USING A CALCULATED DOSE

(71) Applicant: QUANTA DIALYSIS TECHNOLOGIES LIMITED, Warwickshire (GB)

(72) Inventors: Clive Buckberry, Warwickshire (GB); Keith Heyes, Warwickshire (GB); Eduardo Esser, Warwickshire (GB)

(73) Assignee: QUANTA DIALYSIS TECHNOLOGIES LIMITED, Warwickshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,507

(22) Filed: Jan. 24, 2020

(65) Prior Publication Data

US 2020/0330671 A1   Oct. 22, 2020
US 2022/0160943 A9   May 26, 2022

Related U.S. Application Data

(63) Continuation of application No. 15/315,114, filed as application No. PCT/GB2015/051610 on Jun. 2, 2015, now Pat. No. 10,543,305.

(30) Foreign Application Priority Data

Jun. 2, 2014   (GB) ...................................... 1409796

(51) Int. Cl.
*A61M 1/16*   (2006.01)
*C02F 1/02*   (2006.01)
(Continued)

(52) U.S. Cl.
CPC ............. *A61M 1/1686* (2013.01); *A61L 2/04* (2013.01); *A61L 2/24* (2013.01); *A61M 1/1688* (2014.02);
(Continued)

(58) Field of Classification Search
CPC ............. A61M 1/1686; A61M 1/1688; A61M 2205/12; A61M 2205/28;
(Continued)

(56) References Cited

U.S. PATENT DOCUMENTS 2,696,173 A   12/1954   Thormod et al.
3,338,171 A    8/1967   Conklin et al.
(Continued)

FOREIGN PATENT DOCUMENTS

CA         81430 S        8/1997
DE      10024447 A1      11/2001
(Continued)

OTHER PUBLICATIONS

He et al., "A Fluorescent Sensor with High Selectivity and Sensitivity for Potassium in Water," Journal of the American Chemical Society 2003 125 (6), 1468-1469.
(Continued)

*Primary Examiner* — Joseph W Drodge
(74) *Attorney, Agent, or Firm* — Cooley LLP

(57) ABSTRACT

A method of sanitizing liquid for use in a medical device, the method comprising the steps of providing a medical device defining a water circuit with a volume of liquid, sensing the temperature of the volume of liquid with a sensor, heating the volume of liquid from an initial temperature to exceed a threshold temperature, maintaining the volume of liquid above the threshold temperature, determining a time-temperature value for the volume of liquid periodically once the threshold temperature has been exceeded, calculating a
(Continued)

cumulative time-temperature value and providing an output signal once the cumulative time-temperature value has reached a level indicative of a sanitizing dose. A medical device and a liquid sanitizer are also disclosed.

3 Claims, 5 Drawing Sheets

(51) Int. Cl.
  *A61L 2/04* (2006.01)
  *A61L 2/24* (2006.01)
  *C02F 1/00* (2023.01)
  C02F 103/02 (2006.01)

(52) U.S. Cl.
  CPC ............... *C02F 1/008* (2013.01); *C02F 1/02* (2013.01); *A61L 2202/14* (2013.01); *A61L 2202/22* (2013.01); *A61M 2205/12* (2013.01); *A61M 2205/18* (2013.01); *A61M 2205/3368* (2013.01); *A61M 2205/36* (2013.01); *A61M 2205/3653* (2013.01); *A61M 2205/50* (2013.01); *A61M 2205/581* (2013.01); *A61M 2205/583* (2013.01); *C02F 2103/026* (2013.01); *C02F 2209/005* (2013.01); *C02F 2209/02* (2013.01); *C02F 2209/44* (2013.01); *C02F 2303/04* (2013.01)

(58) Field of Classification Search
  CPC ...... A61M 2205/3368; A61M 2205/36; A61M 2205/3653; A61M 2205/50; A61M 2205/581; A61M 2205/583; A61L 2/04; A61L 2/24; A61L 2202/02; A61L 2202/14; B01D 61/28; B01D 61/30; B01D 61/32; B01D 65/02; B01D 65/022; B01D 2313/38; B01D 221/32; C02F 1/008; C02F 1/02; C02F 1/44; C02F 2103/026; C02F 2303/04; C02F 2209/005; C02F 2209/02; C02F 2209/44; G01N 25/00; G01K 3/00; G01K 3/08; G01K 3/10; G01K 13/02; G01K 13/026; G01K 17/06; G01K 17/08
  USPC .... 210/149, 175, 186, 646, 742; 422/28, 38; 604/4.01, 5.01, 6.09, 6.13; 374/29, 102
  See application file for complete search history.

(56) References Cited

U.S. PATENT DOCUMENTS

| | | | |
|---|---|---|---|
| 3,468,261 A | 9/1969 | Schmierer et al. | |
| 3,605,566 A | 9/1971 | Vetter et al. | |
| 3,606,592 A | 9/1971 | Madurski et al. | |
| 3,753,493 A | 8/1973 | Mellor | |
| 3,774,762 A | 11/1973 | Lichtenstein | |
| 3,807,906 A | 4/1974 | Breit | |
| 3,921,622 A | 11/1975 | Cole | |
| 3,972,320 A | 8/1976 | Kalman | |
| 4,070,725 A | 1/1978 | Austin et al. | |
| 4,142,845 A | 3/1979 | Lepp et al. | |
| 4,161,264 A | 7/1979 | Malmgren | |
| 4,205,686 A | 6/1980 | Harris et al. | |
| 4,353,990 A * | 10/1982 | Manske | A61L 2/28 116/207 |
| 4,366,061 A | 12/1982 | Papanek et al. | |
| 4,368,261 A | 1/1983 | Klose et al. | |
| 4,370,983 A | 2/1983 | Lichtenstein | |
| 4,430,048 A | 2/1984 | Fritsch | |
| 4,494,912 A | 1/1985 | Pauliukonis | |
| D277,991 S | 3/1985 | Becker | |
| 4,534,755 A | 8/1985 | Calvert et al. | |
| 4,534,756 A | 8/1985 | Nelson | |
| 4,546,669 A | 10/1985 | Fischer et al. | |
| 4,564,342 A | 1/1986 | Weber et al. | |
| 4,599,165 A | 7/1986 | Chevallet | |
| 4,648,869 A | 3/1987 | Bobo, Jr. | |
| 4,666,598 A | 5/1987 | Heath et al. | |
| 4,710,163 A | 12/1987 | Butterfield | |
| 4,771,792 A | 9/1988 | Seale | |
| 4,828,543 A | 5/1989 | Weiss et al. | |
| 4,897,184 A | 1/1990 | Shouldice et al. | |
| D308,249 S | 5/1990 | Buckley | |
| 4,969,991 A | 11/1990 | Valadez | |
| 5,000,664 A | 3/1991 | Lawless et al. | |
| 5,012,197 A | 4/1991 | Seiffert et al. | |
| 5,032,265 A | 7/1991 | Jha et al. | |
| 5,055,198 A | 10/1991 | Shettigar | |
| 5,095,910 A | 3/1992 | Powers | |
| 5,103,211 A | 4/1992 | Daoud et al. | |
| 5,126,831 A | 6/1992 | Nakagawara | |
| 5,232,434 A | 8/1993 | Inagaki et al. | |
| 5,252,213 A | 10/1993 | Ahmad et al. | |
| D341,890 S | 11/1993 | Sievert et al. | |
| D344,339 S | 2/1994 | Yoshikawa et al. | |
| 5,304,349 A | 4/1994 | Polaschegg | |
| D347,896 S | 6/1994 | Dickinson et al. | |
| D351,470 S | 10/1994 | Scherer et al. | |
| 5,385,540 A | 1/1995 | Abbott et al. | |
| 5,421,823 A | 6/1995 | Kamen et al. | |
| 5,458,468 A | 10/1995 | Ye et al. | |
| 5,476,368 A | 12/1995 | Rabenau et al. | |
| 5,476,792 A * | 12/1995 | Ezrielev | G01K 3/04 116/219 |
| D370,979 S | 6/1996 | Pascale et al. | |
| 5,558,347 A | 9/1996 | Nicholson | |
| 5,586,872 A | 12/1996 | Skobelev et al. | |
| 5,586,873 A | 12/1996 | Novak et al. | |
| 5,591,344 A * | 1/1997 | Kenley | A61L 2/04 210/636 |
| 5,643,201 A | 7/1997 | Peabody et al. | |
| 5,650,071 A | 7/1997 | Brugger et al. | |
| 5,653,456 A | 8/1997 | Mough | |
| 5,658,456 A | 8/1997 | Kenley et al. | |
| 5,665,307 A * | 9/1997 | Kirschner | A61L 2/0088 422/28 |
| 5,727,550 A | 3/1998 | Montecalvo | |
| D395,085 S | 6/1998 | Kenley et al. | |
| 5,788,851 A | 8/1998 | Kenley et al. | |
| 5,807,322 A | 9/1998 | Lindsey et al. | |
| 5,882,300 A | 3/1999 | Malinouskas et al. | |
| 5,948,247 A * | 9/1999 | Gillerfalk | A61M 1/1688 210/175 |
| 5,957,670 A | 9/1999 | Duncan et al. | |
| 5,995,910 A | 11/1999 | Discenzo | |
| 6,077,443 A | 6/2000 | Goldau | |
| 6,126,331 A | 10/2000 | Goldau et al. | |
| 6,132,378 A | 10/2000 | Marino | |
| 6,143,181 A | 11/2000 | Falkvall et al. | |
| 6,153,102 A * | 11/2000 | Kenley | A61L 2/04 210/636 |
| 6,216,029 B1 | 4/2001 | Paltieli | |
| 6,218,329 B1 | 4/2001 | Singh et al. | |
| 6,251,279 B1 | 6/2001 | Peterson et al. | |
| 6,261,065 B1 | 7/2001 | Nayak et al. | |
| 6,303,036 B1 | 10/2001 | Collins et al. | |
| 6,382,923 B1 | 5/2002 | Gray | |
| 6,514,462 B1 * | 2/2003 | Simons | G01K 3/04 116/206 |
| 6,558,347 B1 | 5/2003 | Jhuboo et al. | |
| 6,582,206 B2 | 6/2003 | Schluecker | |
| 6,626,832 B1 | 9/2003 | Paltieli et al. | |
| 6,626,878 B1 | 9/2003 | Leisner et al. | |
| 6,645,176 B1 | 11/2003 | Christenson et al. | |
| 6,663,829 B1 * | 12/2003 | Kjellstrand | A61J 1/2093 422/1 |
| 6,733,476 B2 | 5/2004 | Christenson et al. | |
| 6,743,204 B2 | 6/2004 | Christenson et al. | |
| 6,801,646 B1 | 10/2004 | Pena et al. | |
| 6,814,547 B2 | 11/2004 | Childers et al. | |

(56) References Cited

U.S. PATENT DOCUMENTS

| | | | |
|---|---|---|---|
| 6,967,002 B1* | 11/2005 | Edgson | A61L 2/0023 210/143 |
| 7,040,142 B2 | 5/2006 | Burbank | |
| 7,107,337 B2 | 9/2006 | Lauman et al. | |
| 7,153,286 B2 | 12/2006 | Busby et al. | |
| 7,220,358 B2* | 5/2007 | Schacht | B01D 65/02 210/636 |
| 7,284,964 B2 | 10/2007 | McDowell et al. | |
| 7,434,312 B2 | 10/2008 | Christenson et al. | |
| 7,494,590 B2 | 2/2009 | Felding et al. | |
| 7,604,398 B1* | 10/2009 | Akers | G01K 1/02 374/188 |
| 7,648,627 B2 | 1/2010 | Beden et al. | |
| 7,857,976 B2 | 12/2010 | Bissler et al. | |
| 7,874,999 B2 | 1/2011 | Busby | |
| 7,896,197 B2 | 3/2011 | Furey et al. | |
| D641,882 S | 7/2011 | Hickey et al. | |
| 8,114,043 B2 | 2/2012 | Muller | |
| 8,132,388 B2 | 3/2012 | Nagy et al. | |
| 8,137,184 B2 | 3/2012 | Ajiro et al. | |
| 8,137,300 B2 | 3/2012 | Han et al. | |
| 8,167,431 B2 | 5/2012 | DeCusatis et al. | |
| 8,187,184 B2 | 5/2012 | Muller et al. | |
| 8,192,388 B2 | 6/2012 | Hogard | |
| 8,197,431 B2 | 6/2012 | Bennison | |
| 8,221,320 B2 | 7/2012 | Bouton | |
| 8,348,850 B2 | 1/2013 | Frinak et al. | |
| 8,360,977 B2 | 1/2013 | Marttila et al. | |
| 8,529,490 B2 | 9/2013 | Wariar et al. | |
| 8,535,522 B2 | 9/2013 | Fulkerson et al. | |
| 8,535,525 B2 | 9/2013 | Heyes et al. | |
| D693,469 S | 11/2013 | Chung et al. | |
| 8,597,505 B2 | 12/2013 | Fulkerson et al. | |
| D702,842 S | 4/2014 | Hyde et al. | |
| 8,685,244 B2 | 4/2014 | Heyes et al. | |
| 8,696,571 B2 | 4/2014 | Marttila et al. | |
| 8,708,908 B2 | 4/2014 | Bouton | |
| 8,708,946 B2 | 4/2014 | Han et al. | |
| D705,432 S | 5/2014 | Lura et al. | |
| 8,798,908 B2 | 8/2014 | Bourdeaut | |
| 8,801,646 B2 | 8/2014 | Han et al. | |
| D714,454 S | 9/2014 | Amemiya et al. | |
| D714,946 S | 10/2014 | Lura et al. | |
| 8,926,544 B2 | 1/2015 | Hogard | |
| D724,740 S | 3/2015 | Collins et al. | |
| 8,974,394 B2 | 3/2015 | Frinak et al. | |
| 9,011,334 B2 | 4/2015 | Bouton | |
| D735,868 S | 8/2015 | Mareguddi et al. | |
| 9,220,825 B2 | 12/2015 | Buckberry | |
| D781,410 S | 3/2017 | Ritter et al. | |
| 9,744,285 B2 | 8/2017 | Heyes et al. | |
| 9,833,553 B2 | 12/2017 | Higgitt et al. | |
| 10,456,516 B2 | 10/2019 | Heyes et al. | |
| D867,597 S | 11/2019 | Bauer et al. | |
| 10,543,305 B2* | 1/2020 | Buckberry | C02F 1/008 |
| D879,967 S | 3/2020 | Verguldi et al. | |
| D907,211 S | 1/2021 | Spurling | |
| 10,960,120 B2 | 3/2021 | Wallace et al. | |
| D924,410 S | 7/2021 | Mendoza et al. | |
| D938,046 S | 12/2021 | Gupta et al. | |
| 11,365,728 B2 | 6/2022 | Westenbrink | |
| 2003/0217962 A1* | 11/2003 | Childers | F04B 43/02 210/258 |
| 2004/0195157 A1 | 10/2004 | Mullins et al. | |
| 2004/0206703 A1 | 10/2004 | Bosetto et al. | |
| 2004/0215129 A1* | 10/2004 | Edgson | A61L 2/0023 604/29 |
| 2904/0223857 | 11/2004 | Kline | |
| 2005/0020961 A1 | 1/2005 | Burbank et al. | |
| 2005/0205476 A1 | 9/2005 | Chevallet et al. | |
| 2005/0209547 A1 | 9/2005 | Burbank et al. | |
| 2005/0234384 A1 | 10/2005 | Westberg | |
| 2006/0121623 A1 | 6/2006 | He et al. | |
| 2007/0083193 A1* | 4/2007 | Werneth | A61B 5/7435 606/41 |
| 2008/0200865 A1 | 8/2008 | Bedingfield | |
| 2008/0283096 A1* | 11/2008 | Scheringer | A61L 2/24 134/18 |
| 2009/0007642 A1 | 1/2009 | Busby et al. | |
| 2009/0009290 A1 | 1/2009 | Kneip et al. | |
| 2009/0012450 A1* | 1/2009 | Shah | A61M 1/1686 604/29 |
| 2009/0012452 A1 | 1/2009 | Slepicka et al. | |
| 2009/0012457 A1 | 1/2009 | Childers et al. | |
| 2009/0101550 A1 | 4/2009 | Muller et al. | |
| 2009/0211975 A1 | 8/2009 | Brugger et al. | |
| 2009/0230043 A1 | 9/2009 | Heyes et al. | |
| 2010/0043694 A1* | 2/2010 | Patel | G09F 3/0292 116/201 |
| 2010/0045471 A1 | 2/2010 | Meyers | |
| 2010/0089807 A1 | 4/2010 | Heyes et al. | |
| 2010/0139254 A1 | 6/2010 | Sebestyen et al. | |
| 2010/0263687 A1* | 10/2010 | Braun | A61L 2/18 134/18 |
| 2011/0009797 A1* | 1/2011 | Kelly | A61M 1/1696 604/6.1 |
| 2011/0034850 A1 | 2/2011 | Jonsson | |
| 2011/0132838 A1 | 6/2011 | Curtis et al. | |
| 2011/0168614 A1 | 7/2011 | Pouchoulin et al. | |
| 2012/0164022 A1* | 6/2012 | Muginstein | A61L 2/12 422/22 |
| 2012/0269907 A1 | 10/2012 | Coates | |
| 2012/0276549 A1 | 11/2012 | Cunningham et al. | |
| 2012/0292237 A1 | 11/2012 | Heyes et al. | |
| 2012/0308431 A1* | 12/2012 | Kotsos | A61M 1/1686 422/3 |
| 2013/0037465 A1 | 2/2013 | Heyes et al. | |
| 2013/0056419 A1 | 3/2013 | Curtis | |
| 2013/0153495 A1 | 6/2013 | Kelly et al. | |
| 2013/0199998 A1 | 8/2013 | Kelly et al. | |
| 2013/0274642 A1 | 10/2013 | Soykan et al. | |
| 2014/0224736 A1 | 8/2014 | Heide | |
| 2014/0251885 A1 | 9/2014 | Heyes | |
| 2014/0299544 A1* | 10/2014 | Wilt | F04B 43/14 210/646 |
| 2015/0027951 A1 | 1/2015 | Wallace et al. | |
| 2015/0076053 A1 | 3/2015 | Higgitt et al. | |
| 2015/0112119 A1 | 4/2015 | Buckberry | |
| 2015/0129481 A1 | 5/2015 | Higgitt et al. | |
| 2015/0238673 A1 | 8/2015 | Gerber et al. | |
| 2015/0258263 A1 | 9/2015 | Hogard | |
| 2015/0352269 A1 | 12/2015 | Gerber et al. | |
| 2015/0359954 A1 | 12/2015 | Gerber et al. | |
| 2016/0045656 A1 | 2/2016 | Buckberry | |
| 2016/0051743 A1 | 2/2016 | Buckberry | |
| 2016/0058933 A1 | 3/2016 | Ballantyne et al. | |
| 2016/0077644 A1 | 3/2016 | Ritter et al. | |
| 2017/0056576 A1 | 3/2017 | Doyle et al. | |
| 2017/0167983 A1 | 6/2017 | Klomp et al. | |
| 2017/0252498 A1 | 9/2017 | Heyes et al. | |
| 2017/0296730 A1 | 10/2017 | Soto et al. | |
| 2018/0133391 A1 | 5/2018 | Heyes et al. | |
| 2018/0154059 A1 | 6/2018 | Heyes et al. | |
| 2018/0193545 A1 | 7/2018 | Crnkovich et al. | |
| 2018/0344915 A1 | 12/2018 | Wallace | |
| 2019/0001042 A1 | 1/2019 | Buckberry | |
| 2019/0015577 A1 | 1/2019 | Garrido et al. | |
| 2019/0024654 A1 | 1/2019 | May et al. | |
| 2019/0358381 A1 | 11/2019 | Westenbrink | |
| 2019/0374698 A1 | 12/2019 | Buckberry et al. | |
| 2019/0376504 A1 | 12/2019 | Westenbrink | |
| 2019/0385434 A1 | 12/2019 | Yuds et al. | |
| 2020/0030515 A1 | 1/2020 | Merchant | |
| 2020/0075159 A1 | 3/2020 | Bardorz et al. | |
| 2020/0268958 A1 | 8/2020 | Heyes et al. | |
| 2020/0276372 A1 | 9/2020 | Milad et al. | |
| 2021/0110920 A1 | 4/2021 | Heyes et al. | |
| 2022/0001087 A1 | 1/2022 | Heyes et al. | |
| 2022/0160943 A9 | 5/2022 | Buckberry et al. | |
| 2022/0241480 A1 | 8/2022 | Fincham | |
| 2022/0241573 A1 | 8/2022 | Fincham | |

(56) References Cited

U.S. PATENT DOCUMENTS

FOREIGN PATENT DOCUMENTS

| | | |
|---|---|---|
| EM | EU0043757640001 | 10/2017 |
| EM | EU0043757640002 | 10/2017 |
| EM | EU0079551250002 | 6/2020 |
| EP | 0165751 A2 | 12/1985 |
| EP | 0754468 A2 | 1/1997 |
| EP | 2219703 A1 | 8/2010 |
| EP | 2955512 A1 | 12/2015 |
| FR | 2310136 A1 | 12/1976 |
| GB | 90079551250001 | 5/2020 |
| GB | 90079551250002 | 5/2020 |
| JP | H04266740 | 9/1992 |
| JP | H06261872 | 9/1994 |
| JP | H07174659 A | 7/1995 |
| JP | 2000/130334 | 5/2000 |
| JP | 1645323 S | 11/2020 |
| WO | WO 81/01800 | 7/1981 |
| WO | WO-9100113 A2 | 1/1991 |
| WO | WO-9116542 A1 | 10/1991 |
| WO | WO 95/06205 | 3/1995 |
| WO | WO 95/25893 | 9/1995 |
| WO | WO-9625214 A1 | 8/1996 |
| WO | WO-9710013 A1 | 3/1997 |
| WO | WO-9728368 A2 | 8/1997 |
| WO | WO-9929356 A1 | 6/1999 |
| WO | WO 2000/006217 | 2/2000 |
| WO | WO-0057935 A1 | 10/2000 |
| WO | WO-02066833 A1 | 8/2002 |
| WO | WO-02081917 A1 | 10/2002 |
| WO | WO 2003/101510 | 12/2003 |
| WO | WO-2005044339 A2 | 5/2005 |
| WO | WO-2005080794 A1 | 9/2005 |
| WO | WO 2006/120415 | 11/2006 |
| WO | WO 2006/120417 | 11/2006 |
| WO | WO-2008100671 A1 | 8/2008 |
| WO | WO-2008106191 A1 | 9/2008 |
| WO | WO-2008135245 A1 | 11/2008 |
| WO | WO-2009006489 A2 | 1/2009 |
| WO | WO-2009024333 A1 | 2/2009 |
| WO | WO-2009038834 A1 | 3/2009 |
| WO | WO 2009/061608 | 5/2009 |
| WO | WO-2009127624 A2 | 10/2009 |
| WO | WO-2010089130 A1 | 8/2010 |
| WO | WO-2010146343 A2 | 12/2010 |
| WO | WO-2011027118 A1 | 3/2011 |
| WO | WO-2011068885 A1 | 6/2011 |
| WO | WO-2011105697 A2 | 9/2011 |
| WO | WO-2011105698 A2 | 9/2011 |
| WO | WO 2013/057109 | 4/2013 |
| WO | WO-2013052680 A2 | 4/2013 |
| WO | WO 2013/110906 | 8/2013 |
| WO | WO 2013/110919 | 8/2013 |
| WO | WO 2013/114063 | 8/2013 |
| WO | WO 2013/121162 | 8/2013 |
| WO | WO-2013121163 A1 | 8/2013 |
| WO | WO 2014/072195 | 5/2014 |
| WO | WO-2014082855 A1 | 6/2014 |
| WO | WO 2014/155121 | 10/2014 |
| WO | WO 2015/007596 | 1/2015 |
| WO | WO 2015/022537 | 2/2015 |
| WO | WO 2016/016870 | 2/2016 |
| WO | WO-2017137723 A1 | 8/2017 |
| WO | WO-2018115816 A1 | 6/2018 |

OTHER PUBLICATIONS

Kivi, Air Embolism, Healthline, Aug. 20, 2012, p. 1-5.
Ergo-Express Motorized Dialysis Cart, Aug. 14, 2017, youtube.com [online], [site visited Jan. 9, 2022], Available from internet, URL: https://www.youtube.com/watch?v=j4rAXthOmbY (Year: 2017).
Home Dialysis Tescon Aqua Tech, Aug. 1, 2020, youtube.com [online], [site visited Jan. 9, 2022], Available from internet, URL: https://www.youtube.com/watch?v=WLLPZoS_mz4 (Year: 2020).
LHO2028 Portable Hemodialysis Machine, date unknown, aliexpress.com [online], [site visited Jan. 4, 2022], Available from internet: https://www.aliexpress.com/item/1005003324875329.html?_randl_currency=USD&_randl_shipto=US&src=google&afffcid=1003bab3b8db4e93b9ba88522a14cfc1-1641319351626-05232-UneMJZVf&aff_fsk=UneMJZVf&aff_platform=aaf&sk=UneMJZVf&aff_trace_key= (Year:2022).
Medical Hemodialysis Machine, date unknown, aliexpress.com [online], [site visited Jan. 4, 2022], Available from internet: https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d128cb4801a9ef03ff2 (Year: 2022).
Millenium HX Portable Dialysis Water System, Jul. 2, 2014, youtube.com [online], [site visited Jan. 10, 2022], Available from internet, URL: https://www.youtube.com/watch?v=IGEbPi2CDsw (Year: 2014).
Portable home dialysis device, Nov. 2, 2017, med-technews.com [online], [site visited Jan. 4, 2022], Available from internet: https://www.med-technews.com/news/portable-home-dialysis-device-to-launch-next-year/ (Year: 2017).

* cited by examiner

METHOD OF HEAT SANITIZATION OF A HAEMODIALYSIS WATER CIRCUIT USING A CALCULATED DOSE

RELATED APPLICATIONS

The present application is a continuation of U.S. application Ser. No. 15/315,114, now U.S. Pat. No. 10,543,305, issued Jan. 28, 2020, which is a 371 National Stage filing of PCT application no. PCT/GB2015/051610, filed Jun. 2, 2015 and published as WO2015/185920 on Dec. 10, 2015, which claims foreign priority to GB application no. 1409796.8, filed Jun. 2, 2014. Each of the foregoing disclosures is incorporated herein in its entirety.

The present invention relates to the preparation of dialysis fluid for hemodialysis and related therapies and substitution fluid for use in online therapies, such as hemodiafiltration and hemofiltration. In particular, the present invention relates to a method for heat sanitization of a liquid used in one of the above processes.

It is flown to use heat to destroy microorganisms. During a thermal destruction process, the rate of destruction of microorganisms is logarithmic, as is the rate of growth of the microorganisms. Thus bacteria subjected to heat are killed at a rate that is proportional to the number of organisms present. The process is dependent both on the temperature it exposure and the time required at this temperature to accomplish to desired rate of destruction.

Thermal calculations thus involve the need for knowledge of the concentration of organisms to be destroyed, the acceptable concentration of organisms that can remain behind (spoilage organisms for example, but not pathogens), the thermal resistance of the target organisms (the most heat tolerant ones), and the time-temperature relationship required for destruction of the target organisms.

Disinfection of many water based systems in medical devices is frequently achieved by elevating the temperature for a stipulated period of time, thereby using heat to destroy the microorganism in the water. In dialysis it is common for a combination of 80 degrees Celsius (° C.) to be maintained for 30 minutes.

There are several well-established time-temperature relationships for moist heat disinfection which are regarded as equally acceptable. For moist beat disinfection a particular time at a particular temperature can be expected to have a predictable lethal effect against a standardised population of organisms. It is therefore possible to define a standard exposure which will yield a disinfected product in a correctly operated Washer Disinfector (WD). Actual exposures can then be related to these standard exposure conditions.

Definition of such disinfection processes may be achieved by means of the $A_0$ method which uses a knowledge of the lethality of the particular process at different temperatures to assess the overall lethality of the cycle and express this as the equivalent exposure time at a specified temperature.

The A value is a measure of the heat resistance of a microorganism.

A is defined as the equivalent time in seconds at 80° C. to give a disinfection effect.

The z value indicates the temperature sensitivity of the reaction. It is defined as the change in temperature required to change the A value by a factor of 10.

When the z value is 10° C., the term $A_0$ is used.

The $A_0$ value of moist heat disinfection process is the equivalent time in seconds at a temperature of 80° C. delivered by that process to the product with reference to microorganisms possessing a z value of 10° C.

Where:

$$A_0 = \sum 10\left[\frac{(T-80)}{z}\right]dt$$

$A_0$ is the A value when z is 10° C.;
t is the chosen time interval, in seconds;
and T is the temperature in the load in ° C.

In calculating $A_0$ values a temperature threshold for the integration is set at 65° C. since for temperatures below 65° C. the z and D value of thermophillic organisms may change dramatically and below 55° C. there are a number or organisms which will actively replicate.

In dialysis current practice, raising the temperature to 80° C. for 30 minutes gives a benchmark value $A_0$ equal to 1800.

The present invention aims to provide an efficient method of heat sanitization of a haemodialysis water circuit.

According to the first aspect of the present invention, there is provided a method of sanitizing liquid for use in a medical device, comprising the steps of sensing the temperature of a volume of liquid with a sensor; heating the volume of liquid from an initial temperature to exceed a threshold temperature; maintaining the volume of liquid above the threshold temperature; determining a time-temperature value for the volume of liquid periodically once the threshold temperature has been exceeded; calculating a cumulative time-temperature value; and providing an output signal once the cumulative time-temperature value has reached a level indicative of a sanitizing dose.

Calculation of the time-temperature value for the volume of liquid based on the cumulative effect of heating the water provides a more accurate model of the sanitization process by ensuring a fixed dose of heat sanitization is applied to the volume of liquid. Furthermore, it maximizes the benefits of high temperatures (in particular those above 80° C.) thereby reducing the time for which components are exposed to elevated temperatures. Natural variation in the control loop and water recirculation will cause natural temperature oscillations. Those time periods below 80° C. but above the minimum temperature range are integrated into the dose and those above are not leveraged according to the power law relationship.

The cumulative time-temperature value may be calculated by a processor. Alternatively, the cumulative time-temperature value may be calculated from a lookup table.

The method may comprise the further step of setting a target cumulative time-temperature value and providing the output signal once the target cumulative time-temperature value is reached.

The output signal may be in the form of an audible or visual alarm. This informs the user or operator that the sanitization process is complete.

The output signal may automatically cause termination of the liquid heating. This prevents the heat sanitization cycle from running for longer than is necessary.

The method may comprises the further step of maintaining the volume of liquid below an upper temperature. This may be to prevent boiling of the sanitizing liquid, or prevent unnecessary thermal stress on the components of the heat sanitization device.

The method may comprise the further step of setting the threshold temperature. The method may comprise the further step of setting an overall heating time. This allows the process to be tailored according to the environmental conditions (for example room temperature, liquid input temperature) the situational conditions, (for example emergency procedure, routine procedure, clinic timetables) and the patient's needs. Thus the time and/or temperature may be selected without compromising the dose of heat sanitization applied to the volume of liquid.

The threshold temperature may be between 55° C. and 65° C.

The upper temperature may be between 70° C. and 99° C.

Multiple temperature sensors may be used to provide the temperature of the volume of liquid.

In one embodiment, the cumulative time-temperature value may be calculated according to $$A_0 = \sum 10\left[\frac{(T-80)}{z}\right]dt$$

Where:

$A_0$ is the A value when z is 10° C.;

t is the chosen time interval, in seconds;

and T is the temperature in the load in ° C.

This allows the destruction of organisms at 65° C. to 80° C. to be included in the calculation of the cumulative time-temperature value.

The $A_0$ value may be equal to 1800.

According to a second aspect of the present invention, there is provided a liquid sanitizer comprising a tank containing a volume of liquid; a sensor arranged to sense the temperature of the volume of liquid; a heater arranged to heat the volume of liquid from an initial temperature to exceed a threshold temperature, and maintain the volume of liquid above the threshold temperature; and a processor, wherein the processor is configured to determine a time-temperature value for the volume of liquid periodically once the threshold temperature has been exceeded and calculate a cumulative time-temperature value so as to provide an output signal once a cumulative time-temperature value indicative of a sanitizing dose is reached.

The processor may be programmable to alter at least one of the threshold temperature and the cumulative time-temperature value.

According to a third aspect of the present invention, there is provided a dialyser incorporating the liquid sanitizer according to the second aspect of the present invention.

An embodiment of the present invention will now be described, by way of example only, with reference to the accompanying figures, in which.

Figure 1:
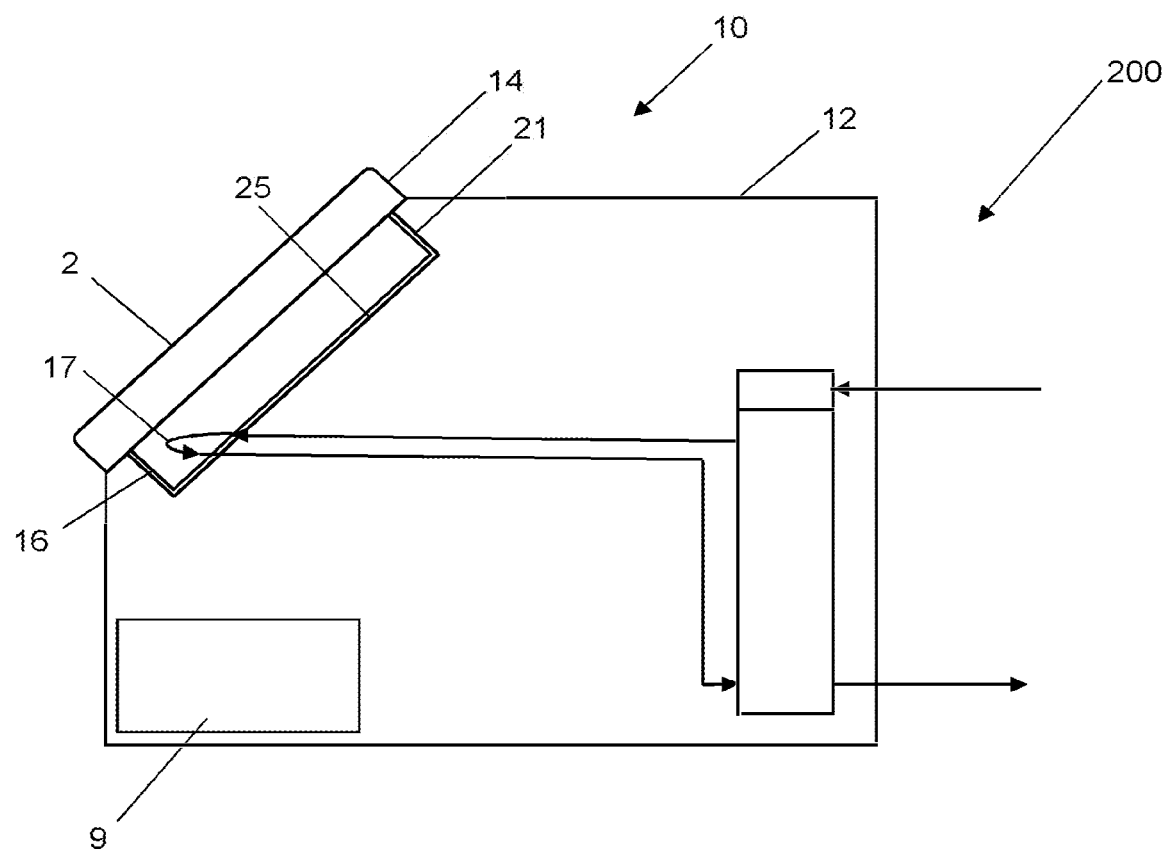
FIG. 1 is a schematic of a dialysis machine incorporating the liquid sanitizer.

Referring to FIG. 1, a dialysis machine 10 is shown having a main body 12 and a hinged door 14. The door 14 is hinged so as to allow a dummy dialysis cartridge 16 to be received between the main body 12 and the door.

The machine 10 has a blood pumping portion indicated generally at 9 for pumping patient blood to and from a dialyser (not shown for clarity) in a known manner. The main body 12 has a platen 21 behind which is an engine portion (not shown for clarity). The platen 21 is configured to receive the dummy cartridge 16 within a recessed portion 25.

The engine portion includes a pneumatic pump for providing pressure and vacuum to operate the machine and a controller to control retention of the dummy cartridge 16 within the machine 10 and fluid flow on the dummy cartridge 16 as will be discussed in further detail below.

The door 14 has an outer side including a user interface 2. The door 14 includes an actuator in the form of an airbag (not shown), operable by the engine portion to provide a closure load to close the dummy cartridge 16 onto the platen 21 and to ensure that a continuous seal fully engages the dummy cartridge 16.

The dummy cartridge 16 will now be described in further detail. The dummy cartridge 16 has a chassis defining a door side and a platen side. In use the platen side of the cartridge 16 engages the platen 21 on the main body 12 of the machine 10, and the door side engages an interface plate (not shown) on the door 14 of the machine 10.

The dummy cartridge 16 is formed from an acrylic such as SG-10 which is moulded in two parts (a platen side and a patient side) before being bonded together to form the chassis. Both the platen side and door side are covered in a clear flexible membrane formed from, for example, DEHP-free PVC which is operable by pneumatic pressure applied to the membrane by the pneumatic compressor in the main body via the platen 21. In this way a series of flow paths 17 are formed in the cartridge for carrying sanitizing water.

In use, the engine portion of the machine 10 applies either a positive or negative pressure to the membrane via the platen 21 in order to selectively open and close valves and pumps to pump sanitizing fluid through the dummy cartridge 16, which is described in detail below.

The machine 10 has liquid sanitizer generally designated as 200. The arrows on FIG. 1 show the sanitizing water flow path when the liquid sanitizer is in use.

Figure 2:
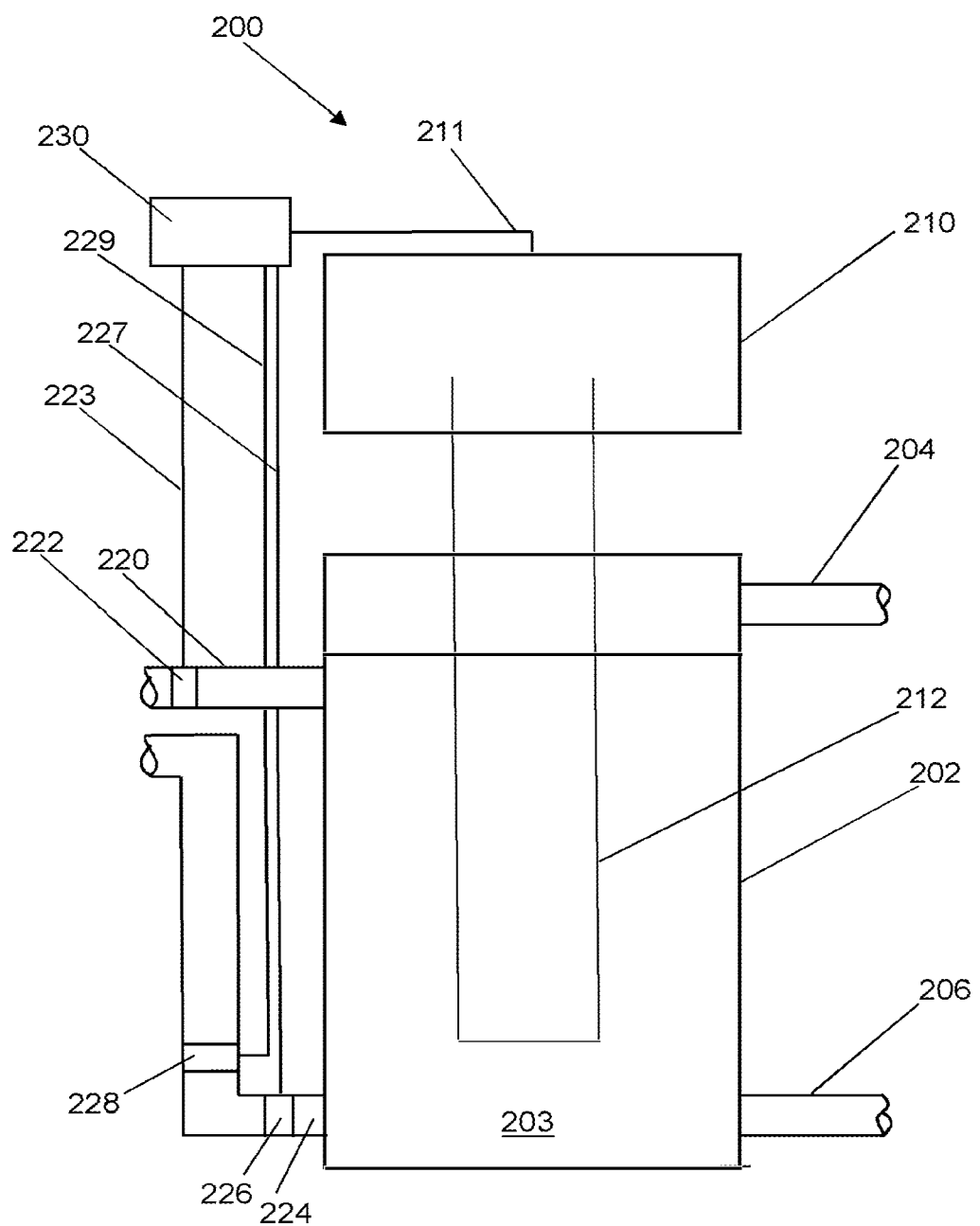
FIG. 2 is a magnified detail view of the liquid sanitzer of FIG. 1.

With reference to FIG. 2, the liquid sanitizer will be described in further detail.

The liquid sanitizer 200 has a tank 202, a heater 210 and a processor 230. The tank 202 contains, in use, a volume of water 203.

The tank 202 has an inlet 204 and a drain 206. The inlet 204 is connectable to a water source (not shown) and the drain 206 is connectable to a waste pipe (also not shown). The tank 202 also has a feed pipe 220 connectable to the dummy cartridge 16 via the platen 21 and a return pipe 224, also connectable to the dummy cartridge 16 via the platen 21. Referring back to FIG. 1, the dummy cartridge 16 has a sanitizing water circulation path 17 so as to complete a sanitizing water circuit comprising the tank 202 feed pipe 220, dummy cartridge 16 and return pipe 224.

The heater 210 has a heating element 212 arranged to heat the volume of water 203 contained within the tank 202, in this case by immersion in the volume of water 203 in the tank 202. The heater 210 is electronically connected to processor 230 by heater connector 211.

Temperature sensors are arranged on the sanitizing water circuit. A driver temperature sensor 222 is arranged on the feed pipe 220 adjacent the water tank 202. A return temperature sensor 226 is arranged on the return pipe 224 adjacent the water tank 202. A check temperature sensor 228 is arranged on the return pipe adjacent, but offset from, the return temperature sensor 226. All three temperature sensors are electronically connected to the processor 230 via sensor connectors. Driver temperature sensor 222 is electronically connected to processor 230 by sensor connector 223. Return temperature sensor 226 is electronically connected to processor 230 by sensor connector 227. Check temperature sensor 228 is electronically connected to processor 230 by sensor connector 229.

The electronic connectors 211, 223, 228, 229 may be wired or wireless. The processor 203 may be remote to both the tank 202 and heater 210.

The processor 230 thereby controls both the heating of the water and receives the temperature values for the sanitizing water circuit.

In use, the tank 202 of liquid sanitizer 200 is filled with the desired quantity of water via inlet 204. This would typically be 500 ml, which is the amount sufficient to flush out the water circuit of a kidney dialyser.

The liquid sanitizer is then turned on. The processor 230 activates the heater 210 to heat the volume of water via the heating element 221 and the pump draws the water around the sanitizing water circuit. The temperature of the water exiting the tank 202 via feed pipe 220 is periodically sensed by drive temperature sensor 222, and the temperature data is periodically sent to processor 230 via sensor connector 223. The temperature of the water returning to the tank 202 via return pipe 224 is periodically sensed by return temperature sensor 226, and the temperature data is periodically sent to processor 230 via sensor connector 227. The processor 230 therefore periodically receives sensed temperature data to provide a feedback loop to moderate the heating of the volume of water 203 to maintain the temperature of the volume of water 203 above a threshold temperature.

When the processor 230 receives data from the sensor 220 that the volume of water 203 has exceeded the threshold temperature, the processor 230 periodically samples the temperature of the volume of water via the return temperature sensor 226, which theoretically represents the lowest possible temperature of the water on the sanitizing water circuit.

The value is checked by periodically sampling the temperature of the volume of water via the check temperature sensor 228.

The sampling is performed periodically at, for example, 1 second intervals. The sampling intervals may be varied as appropriate.

Each sampled temperature represents a time-temperature value, which can be calculated by the processor 230, or alternatively generated by a look-up table.

The processor 230 calculates a cumulative time-temperature value for the volume of liquid 20 by summing the sampled time-temperature values. This is compared to a target total time-temperature value indicative of a sanitizing dose.

Once the calculated cumulative time-temperature value and the target cumulative time-temperature value are equal, the processor 230 sends an output signal to indicate that a sanitizing dose has been reached. The output signal is received by the heater and automatically switches off the heater 210.

In an alternate embodiment, the processor 230 may switch off the water heater 210 in advance of a sanitizing dose being reached, by calculating that there is sufficient thermal energy contained within the water circuit that the water temperature will remain above the threshold temperature for long enough to ensure a sanitizing dose is reached. In that case, periodic sampling would be continued, such that the processor 230 is able to send the output signal to indicate that a sanitizing dose had indeed been reached.

The output signal is received by the LCD display unit, which displays the text "COMPLETE" in reference to the completed sanitizing dose. In alternate embodiments, the LCD display unit includes an audible alarm. The audible alarm can be configured to bleep repeatedly until the sanitizer is turned off.

Figure 3:
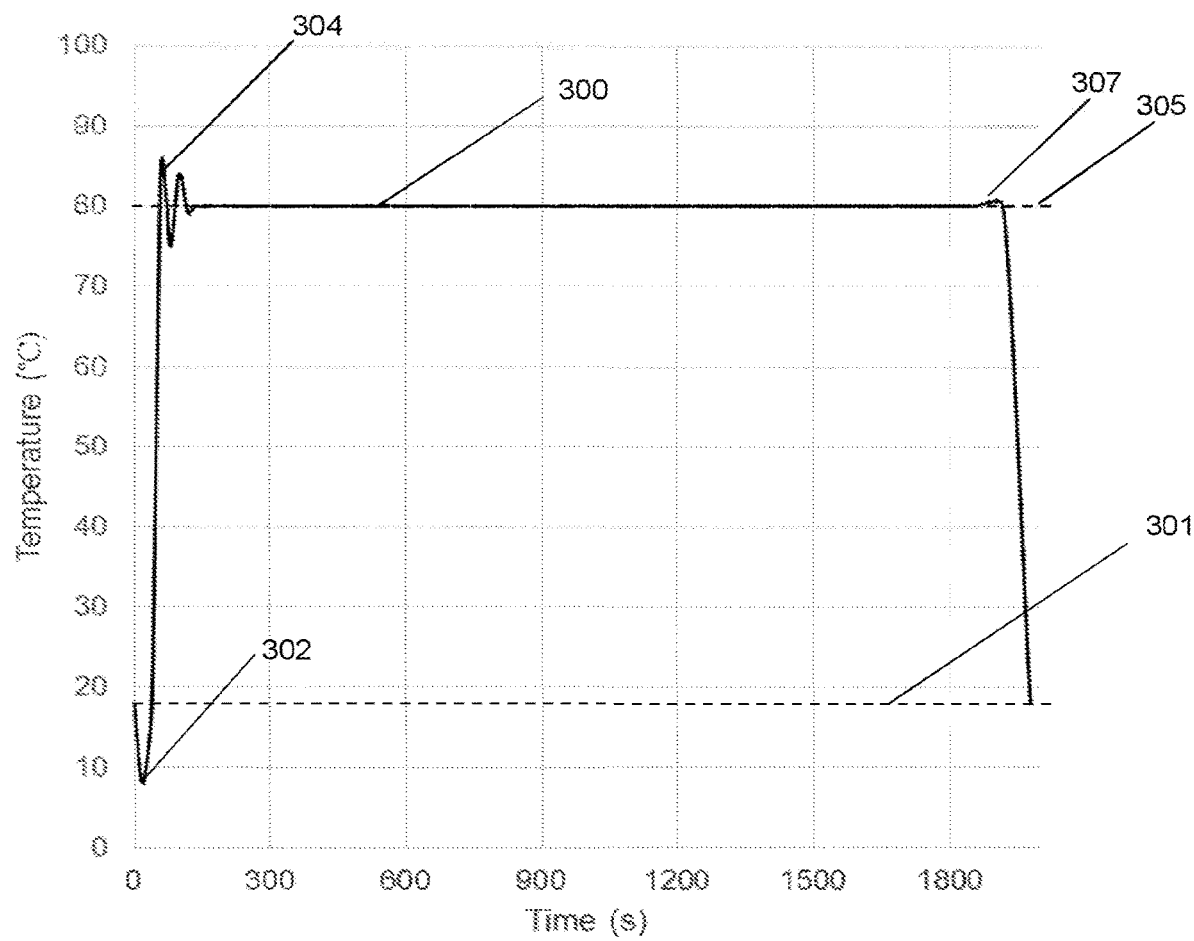
FIG. 3 is a temperature profile of the liquid in a liquid sanitizer undergoing a typical sanitization cycle.

With reference to FIG. 3, a typical temperature profile 300 of the water in a known liquid sanitizer is shown during a single disinfection cycle.

The water already contained within the tank is at room temperature 301 (18° C.) initially. As cool fresh water is added from a tap to ensure the correct quantity of water is provided in the tank (wherein the cool fresh water is typically 8° C.), the overall temperature of the liquid will drop slightly 302.

The water temperature then rises substantially linearly towards the target temperature of 80° C. 305, which is reached at about 60 seconds. There is a slight oscillation 304 of about one and a half wavelengths where the water temperature exceeds and passes below 80° C. (to approximately 85° C. and 75° C. respectively) as the water heater finds the correct balance to maintain a constant water temperature of 80° C. After approximately 30 minutes at 80° C. the water heater is switched off 307 and the water temperature steadily decreases to room temperature (18° C.) 301.

Figure 4:
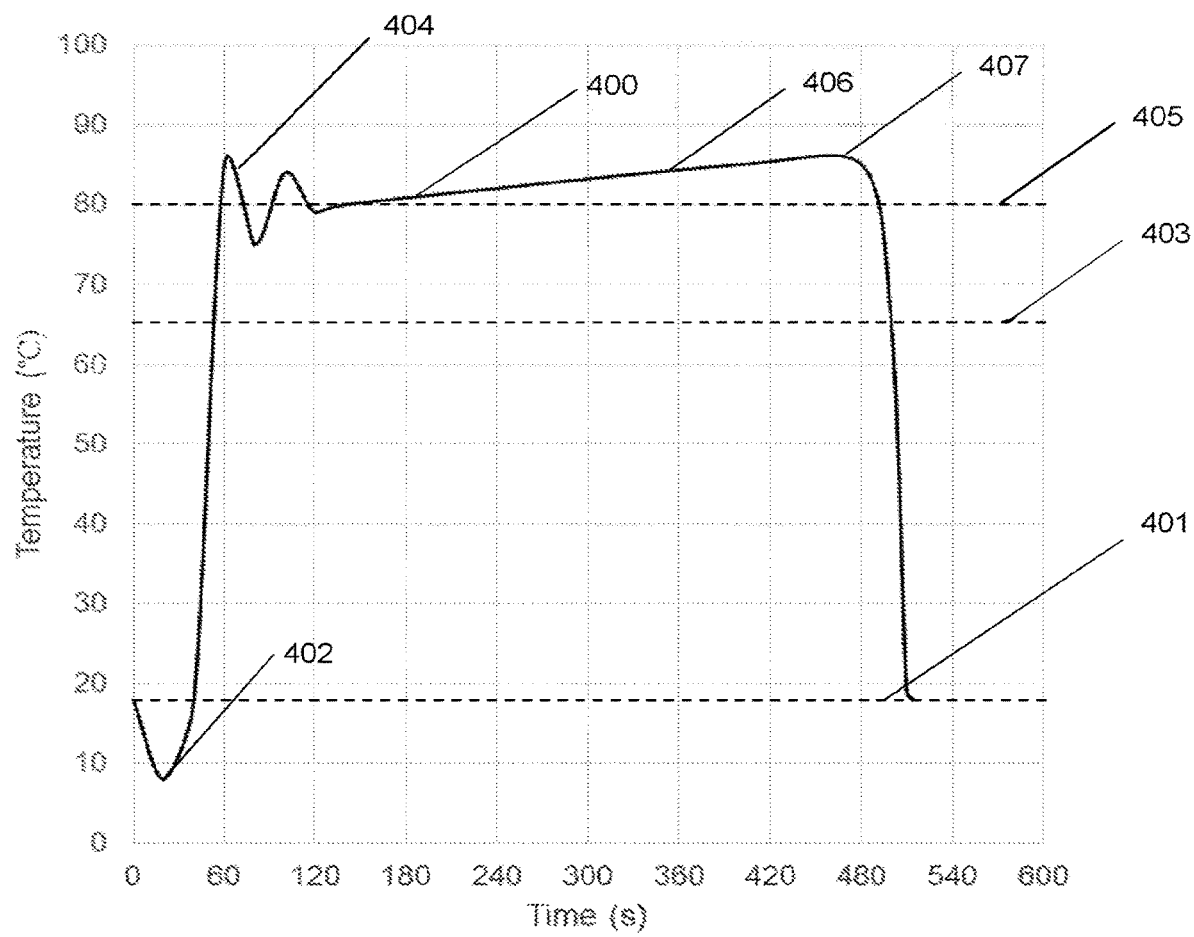
FIG. 4 is a temperature profile of the liquid in the liquid sanitizer of FIG. 1 undergoing a typical sanitization cycle.

With reference to FIG. 4 a typical temperature profile 400 of the water in the liquid sanitizer 200 is shown during a single disinfection cycle.

Similar notable points on the temperature profile are given similar reference numerals as that for FIG. 3, prefixed by a "4" instead of a "3" to indicate that they represent the temperature profile 400 of the water in the liquid sanitizer 200.

The initial drop in temperature 402 from room temperature 401 (18° C.) and subsequent heating of the water occurs following a similar time-temperature profile to that shown in FIG. 3.

However, when the temperature of the water exceeds the threshold temperature. 65° C. 403, the liquid sanitizer begins to record a time-temperature value.

Furthermore, when the target temperature 80° C. 405 is reached, the water temperature is continually raised 406 such that a greater time-temperature value contribution can be achieved with each sample.

The heater is switched off 407 after less than 8 minutes as there is sufficient thermal energy within the water to ensure that a complete sanitizing dose is achieved before the temperature of the water falls below the threshold temperature of 65° C. 403.

The overall cycle time for the sanitizing dose is slightly more than 8 minutes. This compares to the overall cycle time for a sanitizing dose according to the temperature profile of FIG. 3 of over 30 minutes.

An exemplary Lookup Table may include the following values for 1 second sampled increments:

TABLE 1

Lookup Table

| Temperature (° C.) | Time-temperature value |
|---|---|
| 95 | 35.481 |
| 94 | 28.184 |
| 93 | 22.387 |
| 92 | 17.783 |
| 91 | 14.125 |
| 90 | 11.22 |

TABLE 1-continued

Lookup Table

| Temperature (° C.) | Time-temperature value |
|---|---|
| 89 | 8.913 |
| 88 | 7.079 |
| 87 | 5.623 |
| 86 | 4.467 |
| 85 | 3.548 |
| 84 | 2.818 |
| 83 | 2.239 |
| 82 | 1.778 |
| 81 | 1.413 |
| 80 | 1.122 |
| 79 | 0.891 |
| 78 | 0.708 |
| 77 | 0.562 |
| 76 | 0.447 |
| 75 | 0.355 |
| 74 | 0.282 |
| 73 | 0.224 |
| 72 | 0.178 |
| 71 | 0.141 |
| 70 | 0.112 |
| 69 | 0.089 |
| 68 | 0.071 |
| 67 | 0.056 |
| 66 | 0.045 |
| 65 | 0.035 |
| 64 | 0 |

Thus it can be seen that for each 1° C. increase in water temperatures above 80° C., the time-temperature contribution significantly increased. Three seconds at 85° C. is equivalent to over 10 seconds at 80° C.

Figure 5:
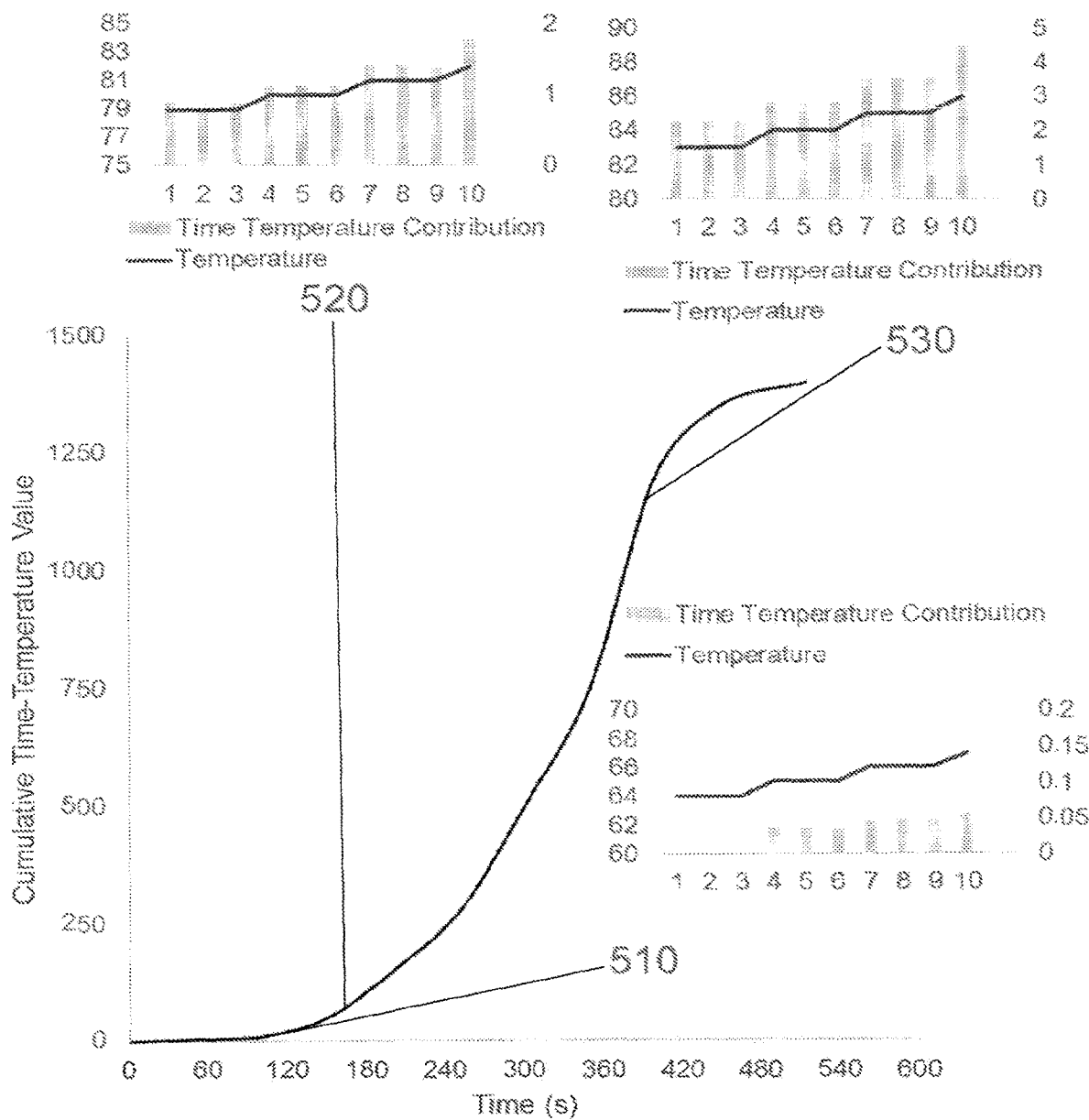
FIG. 5 shows the non-linear contribution to the cumulative time-temperature value, during a single sanitization cycle referred to in the typical temperature profile of FIG. 4.

In FIG. 5, the non-linear contribution to the cumulative time-temperature value, during the single disinfection cycle referred to in the typical temperature profile of FIG. 4, is shown in the main graph. The main graph has the cumulative time temperature value on the Y-axis, and the cycle time (in seconds) on the X-axis. Three distinct periods of 10, one second samples are represented in charts 510, 520, 530, during the disinfection cycle, representing different regions of the main graph. The charts 510, 520, 530 show the time-temperature value contribution for each second according to the temperature sensed during the 1 second intervals.

In chart 510, the 10, one second samples are taken after approximately 50 seconds. During the 10 seconds, the water temperature increases from 64 to 67° C. This is shown by the line graph corresponding to the water temperature Y-axis on the left hand side of the chart. The time temperature contribution at these temperatures is represented by the bars, corresponding to the time temperature Y-axis on the right hand side of the chart.

No contribution is made when the water temperature is 64° C. A relatively small contribution to the time temperature value is made when the water temperature is 65 to 67° C. This corresponds to the flat region of the main graph. Summing the values for the bars indicates that the total contribution of the 10, one second intervals is 0.296. Although these contributions are small, they are counted and do contribute to shorten the time required for sanitization. In the prior art, no credit is given for this heating phase.

In chart 520, the 10, one second samples are taken after approximately 140 seconds. During the 10 seconds, the water temperature increases from 79 to 82° C. This is shown by the line graph corresponding to the water temperature Y-axis on the left hand side of the chart. The time temperature contribution at these temperatures is represented by the bars, corresponding to the time temperature Y-axis on the right hand side of the chart. Note the difference in scale of the time temperature Y-axis of chart 520 to chart 510.

Increasing contributions to the time temperature value are made as the water temperature increases from 79 to 82° C., This corresponds to the steadily increasing region of the main graph. Summing the values for the bars indicates that the total contribution of the 10, one second intervals is 12.056.

In chart 530, the 10, one second samples are taken after approximately 420 seconds. During the 10 seconds, the water temperature increases from 83 to 86° C. This is shown by the line graph corresponding to the water temperature Y-axis on the left hand side of the chart. The time temperature contribution at these temperatures is represented by the bars, corresponding to the time temperature Y-axis on the right hand side of the chart. Note the difference in scale of the time temperature Y-axis of chart 530 to charts 510 and 520.

Greatly increasing contributions to the time temperature value are made as the water temperature increases from 83 to 86° C. This corresponds to the steep region of the main graph. Summing the values for the bars indicates that the total contribution of the 10, one second intervals is 30.282. Counting the actual contribution to sanitization for the periods above 80° C. rather than treating these as the same as 80° C. considerably shortens the required time.

The charts are exemplary in nature only, and different time, temperature and associated time-temperature values are possible, and indeed envisaged.

One second intervals have been chosen as a reasonable sampling rate. The sampling interval could be longer or shorter. A longer sampling interval would preferably be associated with a steady temperature profile, whilst a shorter temperature cycle would preferably be associated with greater processing power.

In alternate embodiments of the liquid sanitizer, the processor may be programmable. Therefore the threshold temperature may be set manually. For example the threshold temperature may be set to a temperature between 55° C. and 65° C. The overall heating time may be set manually. For example, the heating time may be set to 8, 9 or 10 minutes. In this case the processor 230 calculates the necessary temperature profile over the heating time to ensure the volume of water receives a sanitizing dose.

The invention claimed is:

1. A medical device defining a water circuit, the water circuit including:
   a tank containing a volume of liquid;
   a sensor arranged to sense a temperature of liquid, the sensor being arranged on the water circuit on a return line returning liquid to the tank;
   a heater arranged in the tank and configured to heat the volume of liquid from an initial temperature to exceed a threshold temperature, and maintain the volume of liquid above the threshold temperature;
   and
   a processor configured to determine a time-temperature value for the volume of liquid periodically once the threshold temperature has been exceeded and calculate a cumulative time-temperature value so as to provide an output signal once a cumulative time-temperature value indicative of a sanitizing dose is reached.

2. A liquid sanitiser comprising:
   a pneumatic pump;
   a tank containing a volume of liquid;

a sensor arranged to sense a temperature of liquid, the sensor being arranged on a return line returning liquid to the tank;
a heater arranged in the tank and configured to heat the volume of liquid from an initial temperature to exceed a threshold temperature, and maintain the volume of liquid above the threshold temperature;
and
a processor configured to determine a time-temperature value for the volume of liquid periodically once the threshold temperature has been exceeded and calculate a cumulative time-temperature value so as to provide an output signal once a cumulative time-temperature value indicative of a sanitizing dose is reached.

3. The liquid sanitiser of claim 2, wherein the processor is programmable to alter at least one of the threshold temperature and the cumulative time-temperature value.

\* \* \* \* \*